United States Patent [19]

Aronoff et al.

[11] Patent Number: 5,009,648
[45] Date of Patent: Apr. 23, 1991

[54] STARCH CONTAINING FILM OSTOMY POUCHES

[75] Inventors: Marvin S. Aronoff, New York; Denis E. Keyes, Staten Island, both of N.Y.; Robert C. Hahn, Sr., East Brunswick, N.J.

[73] Assignee: E. R. Squibb & Sons, Inc., Princeton, N.J.

[21] Appl. No.: 327,469

[22] Filed: Mar. 22, 1989

[51] Int. Cl.$^5$ ............................................. A61F 5/44
[52] U.S. Cl. .................................. 604/332; 604/338
[58] Field of Search .................. 604/317, 327–353; 524/47, 52, 53; 428/481, 507, 533

[56] References Cited

U.S. PATENT DOCUMENTS

| | | | |
|---|---|---|---|
| 3,339,546 | 9/1967 | Chen | 128/156 |
| 3,934,587 | 1/1976 | Gordon | 604/364 |
| 4,016,117 | 4/1977 | Griffin | 260/17.4 ST |
| 4,021,388 | 5/1977 | Griffin | 260/13 |
| 4,107,426 | 8/1978 | Gordon | 604/375 |
| 4,125,495 | 11/1978 | Griffin | 260/17.4 ST |
| 4,218,350 | 8/1980 | Griffin | 260/17.4 ST |
| 4,324,709 | 4/1982 | Griffin | 523/210 |
| 4,372,311 | 2/1983 | Potts | 128/287 |
| 4,420,576 | 12/1983 | Griffin | 524/47 |
| 4,503,098 | 3/1985 | Potts | 604/381 |
| 4,551,490 | 11/1985 | Doyle et al. | 524/22 |
| 4,620,999 | 11/1986 | Holmes | 428/35 |
| 4,762,738 | 8/1988 | Keyes et al. | 428/36 |
| 4,772,279 | 9/1988 | Brooks et al. | 604/339 |
| 4,868,024 | 9/1989 | Cross et al. | 428/35.2 |

FOREIGN PATENT DOCUMENTS

| | | |
|---|---|---|
| 10171 | 8/1981 | European Pat. Off. . |
| 226439 | 6/1987 | European Pat. Off. . |
| 273611 | 7/1988 | European Pat. Off. . |
| 2083762 | 2/1985 | United Kingdom . |
| 2185404 | 7/1987 | United Kingdom . |
| 2193925 | 2/1988 | United Kingdom . |
| 2195919 | 4/1988 | United Kingdom . |
| 2201372 | 9/1988 | United Kingdom . |
| 2213728 | 8/1989 | United Kingdom . |

OTHER PUBLICATIONS

ASTM-Designation: G21-70 (Reapproved 1980) Standard Practice for Determining Resistance of Synthetic Polymeric Materials to Fungi.
ConvaTec, Active Life One Piece Closed End Ostomy Pouch with Skin Barrier.
Portnoy, "From Cornstarch, A Biodegradable Film", Engineering, Chemical Week/May 27, 1987.
Maddever et al., "Making Plastics Biodegradable Using Modified Starch" Proceedings of Symposium on Degradable Plastics, Society of the Plastics Industry, Jun. 10, 1987, pp. 41–44.
St. Lawrence Starch Co., "Ecostar".

*Primary Examiner*—John D. Yasko
*Assistant Examiner*—Anthony Gutowski
*Attorney, Agent, or Firm*—Stephen B. Davis

[57] ABSTRACT

Biodegradable composite films comprising a starch containing blended polymeric film and a barrier material coated or laminated to the blended film. The use of such composite films in ostomy pouches and other medical products is described. Also described is an ostomy pouch construction in which an adhesive label is affixed to the pouch so as to reduce the escape of odor from the stomal aperture.

15 Claims, 3 Drawing Sheets

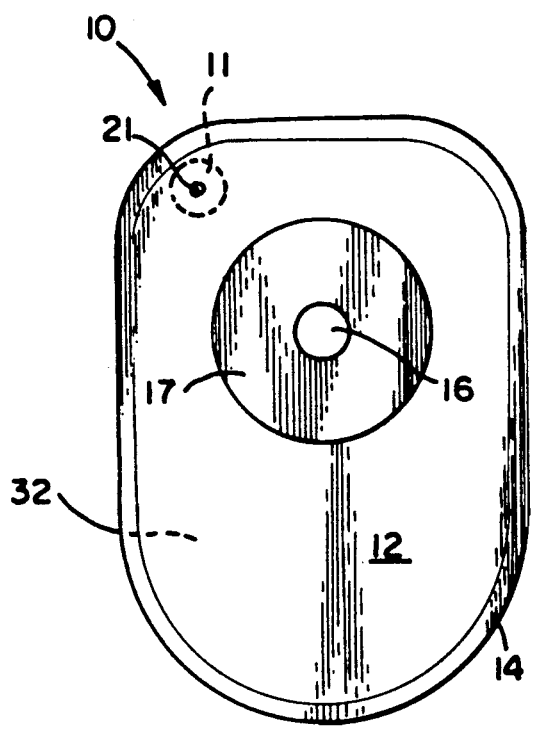
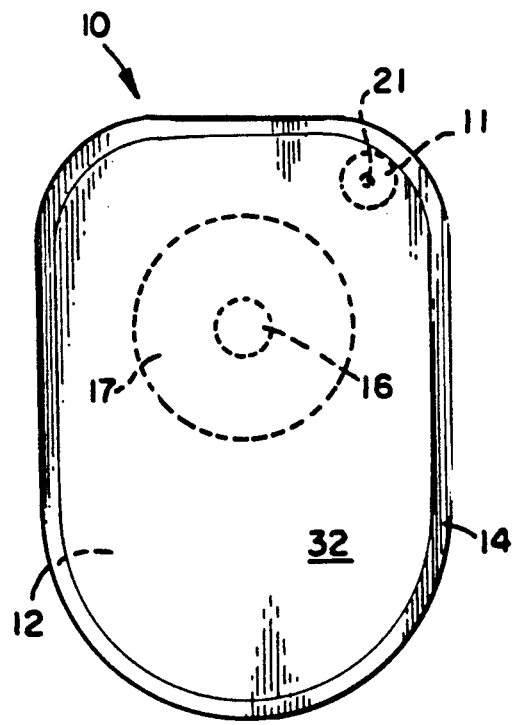
FIG. 1  FIG. 2
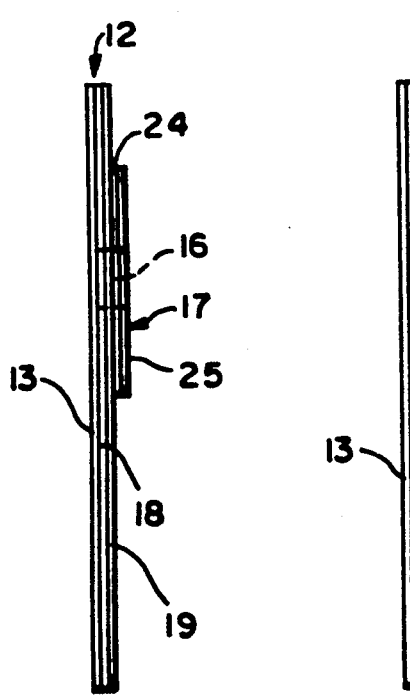
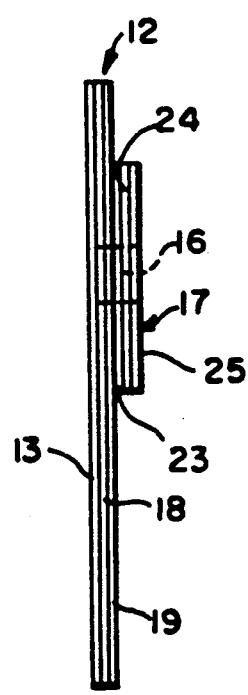
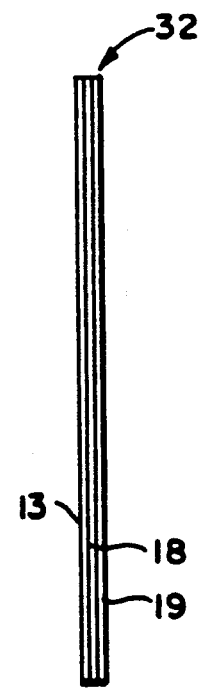
FIG. 3   FIG. 4   FIG. 5

STARCH CONTAINING FILM OSTOMY POUCHES

BACKGROUND OF THE INVENTION

At the present time home use medical products such as ostomy pouches are disposed of by placing the soiled article in a garbage receptacle where it is collected on a daily, bi-weekly, or other regular basis. This method of disposal would be enhanced if the pouch or other device were formed of degradable materials. A further benefit would be obtained if the pouch or other device were sufficiently flexible so that it could be disposed of by flushing in a conventional toilet. Of course, the user must be confident that the device will be flushed and pass through the plumbing system.

Keyes et al. in U.S. Pat. No. 4,762,738 disclose a flushable ostomy pouch made from a laminate of hot water soluble polyvinyl alcohol and water resistant tissue paper. Flushability is increased by incorporating a surfactant within the laminate or adding a surfactant to the toilet water before flushing. Flushability is also increased by wrapping the ostomy pouch in a film or placing the ostomy pouch within a bag or sleeve of polyvinyl alcohol, polyethylene oxide, polypropylene oxide, etc.

Holmes in U.S. Pat. No. 4,620,999 discloses disposable ostomy bags formed from 3-hydroxybutyrate polymers or laminates of polyvinyl alcohol or polyethylene oxide film and 3-hydroxybutyrate. The user must raise the pH of the bag contents to at least 12 prior to disposal.

Martini et al. in European Patent Application 226,439 disclose biodegradable films suitable for use in ostomy pouches consisting of copolymers of beta hydroxy butyric acid and beta hydroxy valeric acid as melt extruded films. This film may be laminated with other films to increase strength or impermeability.

Martini et al. in European Patent Application 273,611 disclose a laminate suitable for a flushable ostomy pouch comprising a laminate of polyvinyl alcohol or polyethylene oxide with a thin coextruded film comprising a melt-bondable layer such as an ethylene vinyl acetate and an impermeable layer such as polyvinylidene chloride.

Brooks et al. in U.K. Patent Application 2,185,404A and U.S. Pat. No. 4,772,279 disclose a flush disposable ostomy pouch having a double sided adhesive faceplate for attachment to the body. The pouch is formed of a laminate of cold water soluble polyvinyl alcohol and polyvinylidene chloride.

Cross et al. in U.K. Patent Application 2,195,919A disclose a laminate which is unaffected by contact with water of neutral pH but is degraded on contact with an alkali added to the toilet bowl. The laminate has a central layer of polyvinyl alcohol, an inner layer made up of at least two coats of a blend of polyvinylidene chloride acrylonitrile copolymer with carboxylated acrylic copolymer and an outer layer of at least two coatings of carboxylated acrylic acid.

Cross et al. in U.K. Patent Application 2,201,372A disclose a flush disposable ostomy bag formed from an inner layer of polyethylene and an outer layer of polyvinyl alcohol. Two flexible layers of aluminium are located between the inner and outer layers to reduce odor transmission.

Kiefer in European Patent No. 10,171B discloses a flushable, disintegratable ostomy pouch made from a multi-layer foil. The inner layer which contacts the body waste is a water-insoluble film-forming material such as polyethylene. The middle layer is of a water soluble material such as polyvinyl alcohol or partially saponified polyvinyl acetate. The outer layer may have water-repellent characteristics and be a material which disintegrates in water when additionally subjected to mechanical means such as kraft paper.

Samways et al. in British Patent No. 2,083,762B disclose a disposable ostomy pouch formed of a composite sheet material comprising an outwardly-presented mechanically strong, backing layer which has good tensile strength and cohesion when dry but which is dissolved or dispersed when immersed in mildly turbulent water and an inwardly-presented mechanically weak but water-impermeable layer. The outer layer can be low wet strength paper or preferably a plastic film such as polyethylene oxide or polyvinyl alcohol. The polyvinyl alcohol may be plasticized and may be a hot-water soluble grade. Materials suitable for forming the water-impermeable layer include polyvinylidene chloride, Saran, nitrocellulose, waxes, pressure sensitive adhesive for example a solution of rubber latex in an organic solvent, etc.

Samways in U.K. Patent Application 2,193,925A discloses a flush disposable sheet material suitable for use as an ostomy bag comprising a 30 to 40 micron water-soluble polyvinyl alcohol film laminated to a 12 to 22 micron water-insoluble polyethylene or polyvinyl chloride film.

Potts in U.S. Pat. Nos. 4,372,311 and 4,503,098 disclose disposable articles made from water soluble polymers coated with a degradable water-insoluble polymer suitable for use in diapers, catamenial devices, sanitary napkins, bandages, etc. The water soluble polymer is selected from poly(alkylene oxide), hydroxyethyl cellulose, hydroxypropyl cellulose, polyvinyl alcohol, polyvinyl pyrrolidone, etc. The degradable water-insoluble polymer is selected from a cyclic ester polymer, a poly ($\beta$-hydroxy butyrate), dialkanoyl polymers, and ethylene polymers.

Griffin in U.S. Pat. Nos. 4,016,117, 4,021,388, 4,125,495, 4,218,350, 4,324,709, and 4,420,576 discloses biodegradable compositions including a synthetic resin and a granular filler such as natural starch.

SUMMARY OF THE INVENTION

This invention is directed to starch containing films and the use of such films in medical products particularly ostomy pouches. The starch containing films of this invention are formed by blending from about 5% to about 50% by weight of the blended film of a natural starch material with a conventional polymeric film material. The resulting film is biodegradable and will break down in a compost heap or landfill. The preferred polymeric film material is ethylene vinyl acetate particularly wherein the vinyl acetate content is from about 9% to about 25% by weight of blended film. Carriers such as low density polyethylene and hydrocarbon waxes and other additives can be included within the blended film. The resulting blended film is then coated with or laminated to an odor and moisture barrier layer to form a composite structure. A preferred barrier is formed by coating the starch containing blended film with polyvinylidene chloride. Depending upon the type product in which the barrier coated or laminated starch containing blended film is employed, layers of other materials can be added to form a multi-layer composite. For example, when the film is in contact with the body such as when the film is made into an ostomy pouch, a comfort ply preferably of moisture absorbent or water proof tissue paper can be laminated to the film to improve the feel on the skin of the user.

Another object of this invention is the construction of a medical device from the composite described above. This composite is particularly suitable for use as the panels of an ostomy pouch since it is soft, pliable, comfortable, and quiet or rattle free when attached to the body of an ostomate. The starch gives the blended film a dry, satiny feel and appearance and more importantly the resulting ostomy pouch is biodegradable. An additional benefit is that the pouch is flexible and can be disposed of by flushing in accordance with the procedures taught by Keyes et al. in U.S. Pat. No. 4,762,738.

Another aspect of this invention is the reduction of odor escaping from ostomy pouches having an adhesive layer or label attached to a ply of non-woven fabric or tissue paper which in turn is sealed to the front pouch panel around the stomal aperture or is the outer layer of the front panel. This is accomplished by including a third film panel on the inside surface of the front pouch panel extending inward of the aperture in the front pouch panel. The adhesive label is then affixed to this inwardly extending portion of the third panel and can also be affixed at its outer periphery to the non-woven fabric or tissue paper. A stomal aperture is provided through the adhesive label and the third film panel to provide access to the pouch interior for the stoma.

BRIEF DESCRIPTION OF THE DRAWINGS

FIG. 1 is a front view of an ostomy pouch constructed from the laminate of this invention as it would be applied to the body of the user.

FIG. 2 is a front view of the rear panel of such ostomy pouch.

FIG. 3 is a side view of the front panel of such ostomy pouch in greatly enlarged detail prior to its being joined to the rear panel but not including the filter element.

FIG. 4 is a side view of a modified front panel of such ostomy pouch in greatly enlarged detail prior to its being joined to the rear panel also not including the filter element.

FIG. 5 is a side view of the rear panel of such ostomy pouch in greatly enlarged detail prior to its being joined to the front panel.

DETAILED DESCRIPTION OF THE INVENTION

Figure 3A:
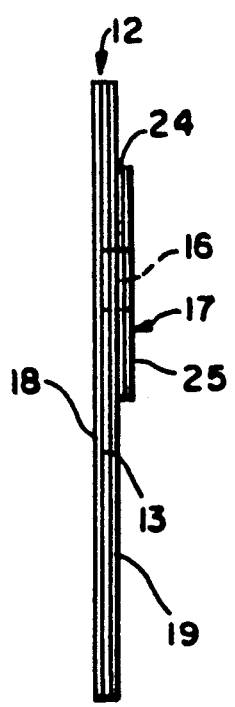
FIG. 3a and 3b are side views similar to FIG. 3 of alternate constructions of the front panel.

This invention is directed to starch containing films which can be coated or laminated with a barrier material. The resulting composite film is degradable in septic systems, landfills, and compost heaps and has properties which make it particularly suitable for use in medical products. For example, the resulting film can be formed into an ostomy pouch, a fecal incontinence pouch, a leg bag for use by a urinary incontinent patient, or a wound drainage receptacle. The film can be employed as the backing layer in a wound dressing or bandage or as the outer wrapper in a diaper or catamenial device.

The starch containing film is formed by blending and forming a film so that the resulting blended film contains from about 5% to about 50% by weight of starch. Suitable polymeric materials with which the starch is blended include polyethylene, polyurethane, ethylene vinyl acetate, nylon, nylon copolymers, N-alkyl substituted nylons and copolymers thereof, polyesters and polyester copolymers, atactic polypropylene, plasticized polyvinyl chloride, copolymers of vinylidene chloride and vinyl acetate, polybutylene, and polyethylmethylacrylate and blends of one or more of these materials.

The starch blended with the polymeric material is a natural starch such as corn starch or rice starch or a blend of the two. The starch can be treated to improve its blending characteristics. For example, the starch can be treated with a silane coupling agent to render it hydrophobic.

Other additives can be incorporated along with the starch into the polymeric film blend. For example, the starch can be added as part of a master blend containing a carrier such as low density polyethylene or hydrocarbon waxes. A particularly useful additive is a material which will promote the ultimate breakdown of the starch blended film after disposal. Such substances are referred to in the Griffin patents, noted above, as autoxidants. In the presence of transition metals such as iron commonly found in landfills these autoxidants are believed to generate peroxides and/or hydroperoxides which initiate the breakdown of the plastic molecule. Suitable autoxidants include unsaturated and polyunsaturated vegetable oils, oleic acid, unsaturated fatty acid ester, and calcium stearamide. Such substances are included in the starch blended film at from about 0.5% to about 8% by weight of blended film.

Other additives can also be incorporated into the starch blended film. For example, drying agents, pigments such as titanium dioxide, as well as additives which are used to increase the stability of the starch, to improve the feel and/or strength of the resulting film, and to assist in converting the blend into a film as taught in the Griffin patents noted previously.

The starch blended film is prepared by blending the polymeric film material or materials, the starch, and any carriers or additives and blowing or casting the blended mixture into a film of desired thickness on a conventional film blowing or casting unit.

A barrier material is coated or laminated to the above described starch blended polymeric film so as to impart added odor and moisture barrier properties. Suitable materials for use as the barrier layer or coating include copolymers and terpolymers of vinylidene chloride, copolymers of vinyl chloride and methyl acrylate, copolymers and terpolymers of vinylidene chloride and vinylidene difluoride, ethylene-vinyl alcohol copolymers, and nylon with polyvinylidene chloride and its copolymers and terpolymers being preferred.

The barrier material can be coated directly onto the surface of the starch blended polymeric film. Alternatively, the barrier material can also be a preformed film which is then bonded to the starch containing film by use of heat, pressure, or adhesive or some combination thereof. Preferably, the barrier material is applied to the starch blended polymeric film as an aqueous emulsion or by other coating procedures. The surface of the starch containing film can be corona treated so as to increase its coatability.

The resulting composite films are suitable for use in medical devices. For example, this film due to its softness, quietness, comfort and feel is ideally suited for use in the manufacture of ostomy pouches. Preferred films within the scope of this invention are prepared by blending a hydrophobic starch along with a carrier such as low density polyethylene plus other additives with ethylene vinyl acetate wherein the resulting blended film will contain from about 7% to about 35% by weight of starch and from about 9% to about 25% by weight of vinyl acetate. Most preferred are such blended films containing from about 15% to about 25% by weight of starch, from about 15% to about 20% by weight of vinyl acetate, up to about 35% by weight of low density polyethylene, and from about 2% to about 6% by weight of an unsaturated oil.

When employed as an ostomy pouch or other bodily waste collection device, the starch blended film will be employed in a thickness of from about 10 to about 100 μm, preferably, from about 15 to about 50 μm. The barrier coating or film will be employed in a thickness of from about 2 to about 25 μm, preferably from about 3 to about 10 μm.

Also, when employed as a pouch, the skin contacting surface may be laminated to a comfort ply so as to improve the feel of the pouch on the body, to absorb perspiration, and to increase the resistance of the barrier coated starch blended film to distortion. Suitable materials for use as the comfort ply include non-woven porous fabrics, open mesh polymeric films, and water absorbent or water proof tissue paper, with tissue paper being the preferred material.

The resulting ostomy pouch made from such laminate in addition to being soft, quiet, and comfortable has the added benefit of being flexible so that it can be disposed of by flushing in accordance with the procedures taught by Keyes et al. in U.S. Pat. No. 4,762,738. Furthermore, the pouch material is degradable when it is deposited in a landfill or compost heap after transit through a municipal sewage system and collection at a sewage treatment plant.

Referring now to the drawings, FIGS. 1 to 7 show an ostomy pouch 10 constructed from the starch containing polymeric film of this invention. This pouch 10 as shown in FIGS. 1 and 2 consists of a first front panel 12 and a second rear panel 32 heat sealed around their periphery to each other by bond 14. The term front panel is used to designate that portion of the pouch which in use is closest to the body.

As best shown in FIG. 1, the front panel includes an opening 16 which functions as a starter hole. The user enlarges this opening by cutting so as to fit the pouch over and around the stoma. Of course, the pouch could be provided with pre-cut openings of various sizes. The stoma can thus protrude into the interior of the pouch. Front panel 12 and rear panel 32 are both formed as a laminate of layers or coatings 13, 18, and 19. Layers 19 are to the exterior of pouch when the front and rear panels are joined. Thus, layers 13 will constitute the pouch interior.

In order for pouch 10 to be suitable for use as an ostomy appliance, it must be capable of maintaining its structural integrity during the normal period of use and must be able to support the normal weight of fecal material that will be discharged into the pouch. For a closed end colostomy pouch, the period of use can extend from several minutes to about 24 hours and the load of the fecal material can be as much as about 250 grams. The pouch must maintain its integrity at body temperature and in the presence of moisture within the fecal material and perspiration that could permeate the pouch from the exterior. Also, the materials employed must result in a pouch having adequate odor barrier properties during use and the materials must be capable of being sealed so as to form the completed pouch. The cost and commercial availability of the materials are also important.

In addition to these properties for the overall pouch, material 19 which in the front panel contacts the body of the user should feel comfortable and non-irritating against skin. Similarly, material 19 in the rear panel contacts the clothing of the user and should therefore also be relatively friction free so as to minimize any pulling on the pouch by clothing which could accidently dislodge the pouch from the body.

Layer 18 in the front and rear panel laminates is the starch containing polymeric film. Layer or coating 13 in the front and rear panel laminates is the barrier material. Layer 19 in the front and rear panel laminates is the comfort ply, preferably water absorbent or waterproof tissue paper.

Figure 5A:
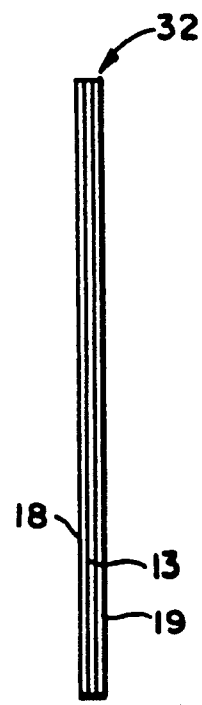
FIG. 5a and 5b are side views similar to FIG. 5 of alternate constructions of the rear panel.
Figure 3B:
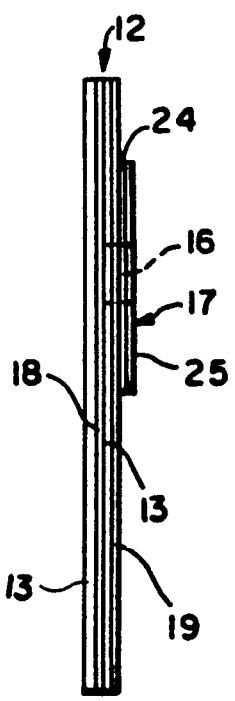
Figure 5B:
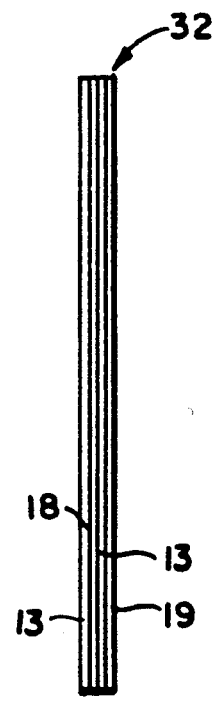

While FIGS. 1 to 7 show panels 12 and 32 as having the barrier layer or coating on one surface of the starch blended film 18 and comfort ply 19 on the other surface, it is possible to construct one or both pouch panels by sandwiching barrier layer or coating 13 between film 18 and comfort ply 19 as shown in FIG. 3a and 5a. This can be done by supporting starch film layer 18 on a substrate, coating or laminating with the barrier material, and then laminating comfort ply 19 to the barrier 13. Also, it is possible to then apply or laminate a second layer of barrier material 13 to the exposed surface of film 18 as shown in FIG. 3b and 5b. All such constructions of panels 12 and 32 are within the scope of this invention.

Attaching means 17 is included on the front pouch panel surrounding the starter hole 16 for attaching the pouch directly or indirectly to the body of the user. Preferably, as shown in figures 1–5, attaching means 17 also has a starter hole 16 and is affixed to the front panel so that the starter holes are aligned. As best shown in FIG. 3 attaching means 17 includes a label or layer of pressure sensitive medical grade adhesive 24 that is capable of forming a bond with the skin of the user of sufficient strength to hold the pouch in place for from several hours to one or more days. The body contacting surface of adhesive label or layer 24 is covered prior to use by a sheet of silicone coated release paper 25. In manufacture, adhesive layer 24 can be applied to the front panel and hole 16 can then be punched through layer 24 and front panel 12.

As shown in FIG. 3 the adhesive layer 24 can be bonded directly to the surface of tissue layer 19 by a combination of heat and pressure. This bond can be strengthened by dusting the surface of adhesive layer 24 with a hot melt powder. Such commercially available materials have little tack at room temperature but when melted develop considerable tack. Alternatively, as shown in FIG. 4, a backing film layer 23 can be interposed between adhesive layer 24 and tissue paper layer 19. Preferably, layer 23 is a thin film of a heat bondable or sealable material such as polyethylene, ethylene vinyl acetate, etc. A seal using heat and pressure is made through the front panel laminate thus bonding layer 23 onto layer 19.

Figure 6:
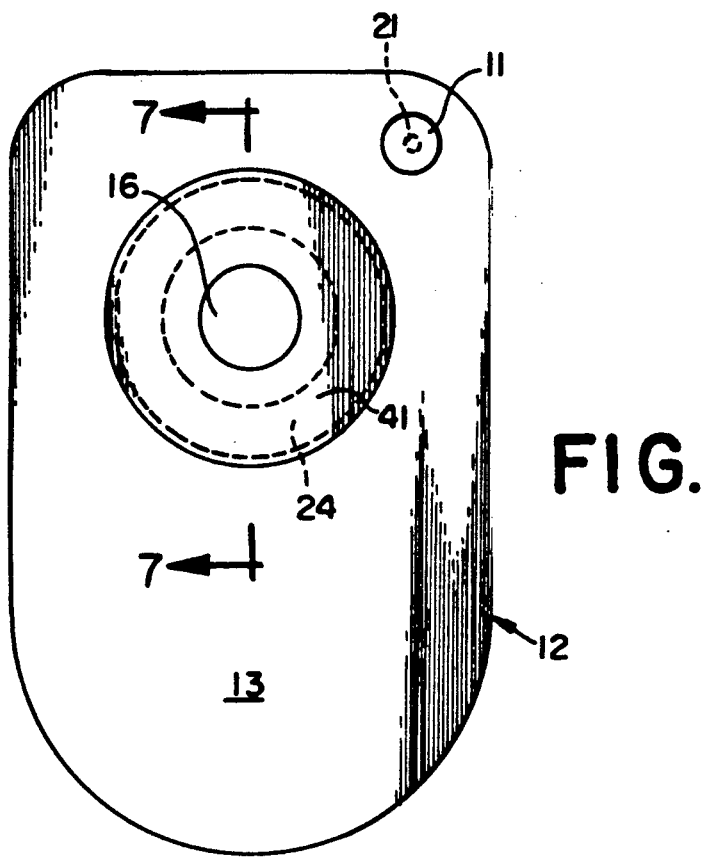
FIG. 6 is a front view of the interior surface of the body side panel of the ostomy pouch prior to its being joined to the rear panel showing an alternate means for securing the attachement means to the pouch.
Figure 7:
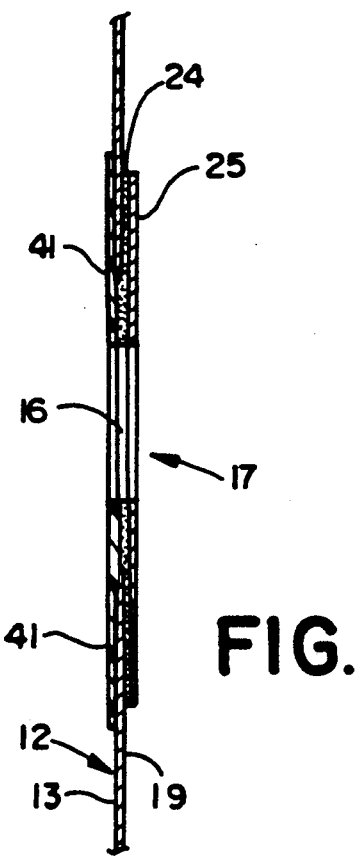
FIG. 7 is a schematic in cross-section of the pouch of FIG. 6 taken along the lines and arrows 7—7 of FIG. 6.

A more preferred manner of bonding adhesive layer 24 to the front pouch panel is shown in FIGS. 6 and 7. The solid line in FIG. 7 represents the composite structure 12 with comfort ply 19 and barrier layer or coating 13 sandwiching the starch containing film layer 18. In this construction, a third panel of starch blended polymeric film 18 coated with barrier material 13 cut in a circular configuration shown as 41 is affixed to the inner surface of front panel 12. The opening in front panel 12 is adjusted to be larger than the stomal opening 16 in panel 41 and adhesive layer 24 so that adhesive layer 24 will bond directly to panel 41 and comfort ply 19 of panel 12. This prevents the migration of odor from the pouch interior through the stomal opening and out through comfort ply 19. Of course, panel 41 can be in other than a circular configuration. Preferably, the surface of panel 41 contacting panel 12 and adhesive label 24 is coated with pressure sensitive adhesive. By so constructing the pouch, adhesive label 24 can be affixed to the front pouch panel without heat or with a minimal amount of heat. Again, aperture 16 can be punched through adhesive layer 24 and third panel 41 after the adhesive layer is applied to panel 41 and comfort ply 19.

As shown in FIG. 1, front panel 12 can also include one or more perforations 21 which are placed to overlie a layer of deodorizing filter material 11. Of course, the perforations could be made in the rear panel in which case the flatus gas would be vented away from the body of the user.

Material 11 preferably contains activated carbon as a gas adsorbing and deodorizing agent. One type of suitable material is a sheet of foamed open-cell non-woven synthetic polymeric material, for example, polyurethane, having a large number of activated carbon particles distributed over one of its major surfaces. Such a material is commercially available under the tradename Bondina. Another type of suitable deodorizing material is a felt pad or paper impregnated with activated carbon in fine particulate form. Various types of such carbon cloths and papers are commercially available.

The pressure sensitive adhesive layer 24 preferably consists of one or more water soluble or swellable hydrocolloids homogeneously dispersed in polyisobutylene as taught by Chen in U.S. Pat. No. 3,339,546. Other suitable hydrocolloid containing pressure sensitive adhesive compositions are taught by Doyle et al. in U.S. Pat. No. 4,551,490. The adhesive mass 24 is preferably extruded between two sheets of silicone coated release paper 25, embodiment of FIG. 3, or is extruded onto a single sheet of silicone coated release paper 25 and overlayed with backing film layer 23, embodiment of FIG. 4. When cooled, this adhesive faceplate is die cut to the circular shape. Starter hole 16 can also be die cut at this time or it can be punched through after the adhesive layer is bonded to the front panel. Of course, the configuration of the adhesive faceplate can be varied from those shown in the drawings. Preferably, adhesive layer 24 is from about 25 to about 35 mils thickness. Backing film layer 23, if present, is from about 0.8 to about 1.5 mils thickness.

The configuration of the ostomy pouch 10 can also be varied from the general eliptical shape shown in the figures. In general, the pouch will vary in width from about 7 to about 10 inches so as to accomodate up to about 300 g. of stomal discharge. The pouch could also be constructed in a smaller size for pediatric use. Of course, instead of the closed end pouch construction shown in the figures, the same laminates could be employed to construct a degradable pouch having a drainable narrow open ended tail portion. This tail portion would then be sealed with a conventional clip type closure during usage.

The ostomy pouch 10 has been shown as having an adhesive means for attachment to the body. However, attaching means 17 could be a mechanical structure of polymeric material adapted to releasably couple the pouch to an adhesive pad secured to the body. This body side pad would be provided with a mechanical structure that couples with the structure on the pouch. Such a mechanical two-piece ostomy coupling system is shown by Steer et al. in U.S. Pat. No. 4,460,363. Thus, the polymeric channel shaped bag coupling element of Steer et al. could be affixed to front panel 12 around starter hole 16 by adhesive or other means. In order for such a pouch to still be degradable and flushable, it may be necessary to remove the coupling member prior to disposal or to form the coupling member from similarly degradable materials.

The ostomy pouch 10 constructed from the starch containing films of this invention are flexible in addition to being degradable. Thus, the pouch 10 can be disposed of as taught by Keyes et al. in U.S. Pat. 4,762,738 by placing the pouch prior to disposal in a flush assist sleeve or bag or wrapping the pouch within a sheet of material that becomes slimy or exudes a slimy material on contact with the water in a toilet bowl. A bag having a plurality of apertures made from an embossed cold water soluble polyvinyl alcohol film (Hi-Selon AH15 from Nippon Gohsei) is suitable as is a bag or sleeve of warm water soluble polyvinyl alcohol (H-211 from Nippon Gohsei).

The pouch construction shown in FIGS. 6 and 7 has application beyond ostomy pouches formed from starch containing films. The escape of odor from an ostomy pouch fabricated from conventional polymeric films where the adhesive label is affixed to a non-woven fabric that in turn is sealed to the front pouch panel about the stoma aperture, can be reduced by employing the construction shown in FIGS. 6 and 7. In this embodiment, third film panel 41 would be of the same conventional film materials as front and rear pouch panels. One surface of panel 41 preferably coated with pressure sensitive adhesive would be affixed to the interior of the front panel and extend inwardly of the aperture in the front panel. The adhesive label would then be affixed to this inwardly extended portion of the third panel. The adhesive label can extend so that its outer portion is then affixed to the non-woven fabric sealed to the front pouch panel around the aperture. A stomal aperture can then be punched or cut through the adhesive layer, release paper, and the third panel. The rear panel is then sealed to the front panel along their peripheral edge to form the completed pouch. This construction prevents or reduces the ability of odor escaping from the stomal aperture to migrate through the non-woven fabric.

EXAMPLE 1

A three component laminate was prepared as follows.

A starch containing film was prepared by blending a master batch composition containing silane treated cornstarch, low density polyethylene, polyunsaturated oil, and calcium oxide (available from St. Lawrence Starch under their tradename Ecostar) with an ethylene vinyl acetate copolymer containing 28% by weight of vinyl acetate (available from C.I.L.). This mixture was blown into a film having a thickness of 32.5 to 35 μm on a conventional film blowing unit. The resulting film contained about 17% (±1%) by weight of vinyl acetate and had a starch level of about 17% (±1%) by weight.

One side of this film was corona treated to a level of 40 dynes in terms of wettability by test oils. A heat seal bonded laminate of this film with a commercially available 2-ply toilet tissue (Erving 3TF2) was prepared by pressing the corona treated side to the tissue paper between nip rollers consisting of a smooth steel roller and a rubber roller. The smooth steel roller was heated to 160° F. and the rubber roller was heated to 140° F. Web speed was approximately 50 ft/minute.

Two coats of a polyvinylidene chloride emulsion were then applied to form a barrier layer. The above laminate was separated from the extra (non-bonded) ply of tissue paper. The ethylene vinyl acetate starch containing film side was passed through a corona treater to produce wettability in the range of 40–60 dynes (corona discharge output was in the range of 0.25 to 0.45 kilowatt). The laminate was then run through a Faustel pilot coating unit at a web speed of 20–40 ft/min. A polyvinylidene chloride-acrylate polymer emulsion containing about 60% by weight solids (Unocal 5518) mixed with about 10% by weight of a 50/50 weight/weight isopropanol-water solution was then applied with a 130 quad cell gravure roll to the corona treated surface. The quantity of emulsion remaining on the film was controlled by use of conventional Meier rods (#3 rods).

The web was then passed through a drying oven approximately 20 ft. long heated to 115°–175° F. Similar conditions were used in the second coat except that there was no corona treatment. The total polyvinylidene chloride coating applied was 4.5 to 5 lbs./3000 ft.$^2$.

The resulting three component laminate was soft and supple. Oxygen transmission of the three component laminate was 2.5 to 5.0 cc./100 in.$^2$/24 hours.

EXAMPLE 2

The three component laminate from Example 1 and the starch containing ethylene vinyl acetate film were tested for biodegradability according ASTM G 21-70. According to this procedure strips of these materials were inoculated with 5 test fungal spores in a medium devoid of a carbon source.

At the end of 21 days the inoculated paper side of the laminate was covered by fungus. Examination of the film surface under the paper by scanning electron microscopy showed a zone where cracking had occurred, suggesting embrittlement due to breakdown of the polymer matrix in this area. Break elogation in the machine direction was 65% of the initial value, also suggesting embrittlement was occurring.

Discrete fungal colonies grew on the surface of the unlaminated film, indicating some degree of biodegradation.

The three component laminate from Example 1 was also subjected to conventional field composting conditioned. At the end of four weeks, the laminate retained 35% of its initial strength when tested in the machine direction and 53% in the transverse direction, indicating breakdown under composting conditions. At the end of six weeks the samples had deteriorated to the point where they could no longer be separated from the composting heap.

In another series of such composting tests this laminate lost up to 89% of its burst strength after 24 weeks. The laminate was severely discolored, had holes and cracks in the starch containing film and was partly embrittled.

EXAMPLE 3

Closed end ostomy pouches having the general configuration shown in FIGS. 1, 2, 3 and 5 were prepared as follows. Front and rear panels were cut from the three component laminates described in Example 1. In the front panel, an opening 16 of about 18 mm. was cut. A small hole 21 was punched and a carbon containing filter 11 was adhesively attached to the polyvinylidene chloride side of the front panel laminate over opening 21.

Attaching means 17 was prepared as follows. Layer 24 consists on a weight percent basis of the following ingredients:

| | |
|---|---|
| Sodium carboxymethylcellulose | 22.17 |
| Gelatin | 22.17 |
| Pectin | 22.16 |
| Polyisobutylene(available from Exxon as Vistanex LM-MH) | 9.5 |
| Polysiobutylene(available from Exxon as Vistanex L-100) | 9.5 |
| Mineral oil | 14.5 |

A premix of the two grades of polyisobutylene was prepared by masticating the L-100 to a fine shred in a Sigma blade mixer and blending with the LM-MH. A weighted amount of this premix was then placed into a mixer and a powdery blend of the gelatin, pectin, and sodium carboxymethylcellulose was added. Mixing was continued and the mineral oil was gradually added and incorporated into the mass. The mass was heated to 180° to 190° F. and extruded between two sheets of silicone coated release paper. The adhesive layer 24 was a thickness of about 25 mils. The resulting attaching means 17 was cut into shape with an opening corresponding to stomal aperture 16. One sheet of release paper was removed and the exposed surface of adhesive mass 24 was dusted with a hot melt powder (Avabond 6652 modified). The attaching means was then affixed to tissue paper layer 19 of the front panel laminate by a combination of heat and pressure.

The front and rear panels were then heat sealed together around their periphery with the polyvinylidene chloride layers 13 facing one another.

EXAMPLE 4

Pouches of the type described in Example 3 were tested for flushability. These pouches differed from those described in Example 3 in that the starch containing film was a laminate of an ethylene vinyl acetate and 16% by weight of starch (30 μm thick) coated with polyvinylidene chloride (Unocal 528F), and heat seal laminated to a ply of absorbent tissue paper. Also, the pouches tested did not include a filter.

The following table shows that the pouches constructed from the starch containing films of this invention were sufficiently pliable and flexible to be reliably disposed of by flushing when lubricity is added. This was done by placing the pouch prior to flushing in a bag formed from an embossed cold water soluble polyvinyl alcohol film (15 micron thick film of Hi-Selon AH-15 from Nippon Gohsei).

In this experiment, the fecal load was simulated by a blend of meat type dogfood and agar.

The toilet was flushed immediately after the pouch or bag containing the pouch were placed therein. The pouch was considered to have successfully flushed if it passed from the bowl and trap in three flushes or less and a failure if the water rose to or beyond the level of the rim of the toilet or if the pouch failed to clear the bowl and trap after the third flush. Also noted were any instances of transient blockage of the pouch in the toilet system which cleared due to increased head from water back up in the bowl, i.e., spontaneous release.

These pouches loaded with 150 g. of the above fecal model were stored in a functioning septic tank. After 130 days, material removed from the side of the pouch was treated in the machine direction. It retained 84.4% of its initial tensile strength indicating some degradation had occurred.

| | Mansfield Syphon Jet (3.5 gallon tank) | | |
|---|---|---|---|
| Load | Pass rate | Number of passes requiring multiple flushes | Number of passes with spontaneous release |
| Pouch-Bag Combination | | | |
| 200 g. + 50 cc. of water | 11/11 | — | — |
| 200 g. | 10/10 | 1 | 4 |
| 150 g. | 10/10 | — | — |
| 25 g. | 10/10 | 1 | — |
| no load | 5/5 | 1 | 1 |
| Pouch Alone | | | |
| 150 g. | 1/5 | — | — |
| no load | 5/5 | 2 | — |

| | Douglas-Leader Washdown Syphon Jet (5 gallon tank) Punch-Bag Combination | | |
|---|---|---|---|
| Load | Pass rate | Number of passes requiring multiple flushes | Number of passes with spontaneous release |
| 200 g. + 50 cc. of water | 10/10 | — | — |
| 200 g. | 9/10 | — | — |
| 150 g. | 10/10 | 2 | — |
| 25 g. | 10/10 | 2 | — |
| no load | 5/5 | — | — |

EXAMPLE 5

Pouches of the type employed in Example 4 were also tested for flushability in a European washdown toilet system. The toilet employed was a Twyfords B5 P-trap with a 9.1 liter flush.

In this test, the top of each pouch was manually torn open prior to flushing or prior to placement within the flush assist bag. In this example, the flush assist bag was formed from a warm water soluble polyvinyl alcohol film (25 micron thick film of Nippon Gohsei H-211) having a plurality of horizontal slits.

The fecal load was simulated by a 150 g. blend of meat type dogfood and agar.

In this experiment 5 pouches required 13 flush attempts to clear the pan. When the pouch was used in combination with the flush assist bag, the combination cleared the pan after one flush in 37 out of 37 attempts.

What is claimed is:

1. An ostomy pouch comprising a first front panel and a second rear panel sealed together along at least a portion of their periphery to form said pouch, said first front panel having an aperture providing access to the pouch interior for the stoma of the user, both said first front panel and said second rear panel formed of a composite film comprising a starch containing blended polymeric film coated on one surface with a barrier of polyvinylidene chloride and a ply of water absorbent or waterproof tissue paper laminated to the other surface of said starch containing blended polymeric films, said tissue paper plies constituting the exterior surface of said pouch, an adhesive label affixed to the tissue paper ply of said first front panel around said stomal aperture, and wherein said starch blended polymeric films comprise from about 15% to about 25% by weight of hydrophobic starch, ethylene vinyl acetate wherein each starch blended polymeric film contains from about 15% to about 20% by weight of vinyl acetate, up to 35% by weight of low density polyethylene, and from about 2% to about 6% by weight of an unsaturated vegetable oil.

2. An ostomy pouch of claim 1 wherein said starch blended polymeric films are from about 15 to about 50 μm in thickness and said barrier coatings are from about 3 to about 10 μm in thickness.

3. An ostomy pouch comprising a first front panel and a second rear panel sealed together along at least a portion of their periphery to form said pouch, said first front panel having an aperture, both said first front panel and said second rear panel formed of a composite film comprising a starch containing blended polymeric film coated on one surface with a barrier of polyvinylidene chloride and a ply of water absorbent or water proof tissue paper laminated to the other surface of said starch containing blended polymeric films, said tissue paper plies constituting the exterior surface of said pouch, a third panel affixed to the inner surface of said first front panel and extending into the area of said first front panel aperture, said third panel formed of a composite film comprising a starch blended polymeric film coated on one surface with a barrier of polyvinylidene chloride, an adhesive label affixed to the portion of said third panel extending into the area of said first front panel aperture and also affixed to a portion of the tissue paper ply of said first front panel around said first front panel aperture, a stomal aperture through said adhesive label and said third panel to provide access to the pouch interior, and wherein said starch blended polymeric films comprise from about 15% to about 25% by weight of hydrophobic starch, ethylene vinyl acetate wherein each starch blended polymeric film contains from about 15% to about 20% by weight of vinyl acetate, up to 35% by weight of low density polyethylene, and from about 2% to about 6% by weight of an unsaturated vegetable oil.

4. An ostomy pouch of claim 3 wherein said starch blended polymeric films are from about 15 to about 50 μm in thickness and said barrier coatings are from about 3 to about 10 μm in thickness.

5. An ostomy pouch comprising a first front panel and a second rear panel sealed together along at least a portion of their periphery to form said pouch, said first front panel having an aperture providing access to the pouch interior for the stoma of the user, and attachment means affixed to said first front panel around said aperture for securing the pouch to the body of the user, said first front panel and said second rear panel both formed of a composite film comprising a starch containing blended polymeric film of from about 7% to about 35% by weight of a hydrophobic starch, ethylene vinyl acetate and optionally one or more additional polymeric materials selected from the group consisting of polyethylene, polyurethane, nylon, nylon copolymers, N-alkyl substituted nylons and copolymers thereof, polyesters, polyester copolymers, atactic polypropylene, plasticized polyvinyl chloride, copolymers of vinylidene chloride and vinyl acetate, polybutylene, and polyethylmethylacrylate wherein each blended film contains from about 9% to about 25% by weight of vinyl acetate, and from about 0.5% to about 8% by weight of one or more autoxidants selected from the group consisting of unsaturated vegetable oils, polyunsaturated vegetable oils, oleic acid, unsaturated fatty acid esters, and calcium stearamide, and a barrier material selected from the group consisting of copolymers of vinylidene chloride, terpolymers or vinylidene chloride, copolymers of vinyl chloride and methyl acrylate, copolymers of vinylidene chloride and vinylidene difluoride, terpolymers of vinylidene chloride and vinylidene difluoride, ethylenevinyl alcohol copolymers, and nylon coated on or laminated to said starch containing polymeric film.

6. An ostomy pouch of claim 5, wherein each of said starch blended polymeric films also contain low density polyethylene, said autoxidant in each blended polymeric film is an unsaturated vegetable oil, and said barrier material in each composite film is polyvinylidene chloride, a copolymer of polyvinylidene chloride, or a terpolymer of polyvinylidene chloride.

7. An ostomy pouch of claim 6 wherein each of said starch blended polymeric films comprise from about 15% to about 25% by weight of hydrophobic starch, ethylene vinyl acetate wherein each blended film contains from about 15% to about 20% by weight of said vinyl acetate, up to 35% by weight of low density polyethylene, and from about 2% to about 6% by weight of said unsaturated vegetable oil.

8. An ostomy pouch comprising a first front panel and a second rear panel sealed together along at least a portion of their periphery to form said pouch, said first front panel having an aperture providing access to the pouch interior for the stoma of the user, and attachment means affixed to said first front panel around said aperture for securing the pouch to the body of the user, said first front panel and said second rear panel both formed of a composite film comprising an interior barrier material coated or laminated to a starch containing blended polymeric film of from about 5% to about 50% by weight of starch and one or more polymeric materials selected from the group consisting of polyethylene, polyurethane, ethylene vinyl acetate, nylon, nylon copolymers, N-alkyl substituted nylons and copolymers thereof, polyesters, polyester copolymers, atactic polypropylene, plasticized polyvinyl chloride, copolymers of vinylidene chloride and vinyl acetate, polybutylene and polyethylmethylacrylate, a second barrier material coated or laminated to the opposite surface of said starch containing blended polymeric film, and a comfort ply laminated to said second barrier materials wherein said comfort plies constitute the exterior surface of said pouch.

9. An ostomy pouch of claim 8 wherein each of said plies is water absorbent or water proof tissue paper.

10. An ostomy pouch of claim 8 wherein said interior barrier material and said second barrier material of each of said composite films is selected from the group consisting of copolymers of vinylidene chloride, terpolymers of vinylidene chloride, copolymers of vinyl chloride and methyl acrylate, copolymers of vinylidene chloride and vinylidene difluoride, terpolymers of vinylidene chloride and vinylidene difluoride, ethylenevinyl alcohol copolymers, and nylon.

11. An ostomy pouch of claim 10 wherein each of said starch containing blended polymeric films also contains one or more autoxidants selected from the group consisting of unsaturated vegetable oils, polyunsaturated vegetable oils, oleic acid, unsaturated fatty acid esters, and calcium stearamide.

12. An ostomy pouch comprising a first front panel and a second rear panel sealed together along a least as portion of their periphery to form said pouch, said first front panel having an aperture providing access to the pouch interior for the stoma of the user, and attachment means affixed to said first front panel around said aperture for securing the pouch to the body of the user, said first front panel and said second rear panel both formed of a composite film comprising a starch containing blended polymeric film of from about 5% to about 50% by weight of starch and one or more polymeric materials selected from the group consisting of polyethylene, polyurethane, ethylene vinyl acetate, nylon, nylon copolymers, N-alkyl substituted nylons and copolymers thereof, polyesters, polyester copolymers, atactic polypropylene, plasticized polyvinyl chloride, copolymers of vinylidene chloride and vinyl acetate, polybutylene, and polyethylmethylacrylate, a barrier material coated or laminated to one surface of each of said starch containing polymeric films, and a comfort ply laminated to the exposed surface of said barrier materials thus sandwiching said barrier materials between said starch containing polymeric films and said comfort plies, and wherein said comfort plies constitutes the exterior surface of said pouch.

13. An ostomy pouch of claim 12 wherein each of said comfort plies is a water absorbent or water proof tissue paper.

14. An ostomy pouch of claim 12 wherein the barrier material of each of said composite films is selected from the group consisting of copolymers of vinylidene chloride, terpolymers of vinylidene chloride, copolymers of vinyl chloride and methyl acrylate, copolymers of vinylidene chloride and vinylidene difluoride, terpolymers of vinylidene chloride and vinylidene difluoride, ethylenevinyl alcohol copolymers, and nylon.

15. An ostomy pouch of claim 14 wherein each of said starch containing blended polymeric films also contains one or more autoxidants selected from the group consisting of unsaturated vegative oils, polyunsaturated vegetable oils, oleic acid, unsaturated fatty acid esters, and calcium stearamide.

* * * * *